(12) United States Patent
Frumker et al.

(10) Patent No.: US 6,961,121 B1
(45) Date of Patent: Nov. 1, 2005

(54) METHOD AND SYSTEM FOR EVALUATING OPTICAL DISTURBANCES OCCURRING IN A SUPERSONIC FLOW FIELD

(75) Inventors: Evgeny Frumker, Beer Sheva (IL); Ofer Pade, Haifa (IL)

(73) Assignee: Rafael-Armament Development Authority Ltd., Haifa (IL)

( * ) Notice: Subject to any disclaimer, the term of this patent is extended or adjusted under 35 U.S.C. 154(b) by 284 days.

(21) Appl. No.: 10/461,487

(22) Filed: Jun. 16, 2003

(30) Foreign Application Priority Data

Jun. 16, 2002 (IL) ..................................... 150243

(51) Int. Cl.$^7$ ............................................. G01N 21/41
(52) U.S. Cl. ................. 356/128; 356/124.5; 250/201.9
(58) Field of Search .............................. 356/128, 124.5, 356/73; 250/201.9; 359/554, 557; 702/3, 702/4; 340/601, 602, 905, 7.48, 962, 968

(56) References Cited

U.S. PATENT DOCUMENTS 6,552,318 B1 * 4/2003 Crowther et al. ......... 250/201.9

OTHER PUBLICATIONS

G. W. Sutton, "Aero-optical Foundations and Applications", AIAA Journal, vol. 23, No. 10, Oct. 1985, p. 1525-1537.
Robert J. Renka, "Multivariate interpolation of large sets of scattered data", ACM Transactions on Mathematical Software vol. 14 No. 2 pp. 139-148 (Jun. 1988).
Gladstone-Dale formula (J. H. Gladstone and T. P. Dale, Trans. Roy. Soc. London vol. 153 pp. 317-337 (1863).
H. H. Hopkins, "Geometrical-optical treatment of frequency response", Proc. Phys. Soc. vol. 70B p. 1002-1005 (1957).
Fluent manual dated Dec. 2001, pp. 25-117 to 25-119, incorporated herein by reference, output available from Fluent6 includes "XY plot files".
Operating CodeV v.9.0 Reference Manual, vol. 1 (Sep. 2001) p. 1A-107 and p. 1A-121.
Warren J. Smith, Modern Optical Engineering (McGraw Hill, 2000).

* cited by examiner

Primary Examiner—Gregory J. Toatley, Jr.
Assistant Examiner—Roy M. Punnoose
(74) Attorney, Agent, or Firm—Mark M. Friedman

(57) ABSTRACT

A method of evaluating optical disturbances occurring in a flow field around a solid body. The method includes performing a computational fluid dynamics (CFD) calculation to obtain a three-dimensional index-of-refraction field outside the solid body, and performing one or more ray tracing calculation based on the sindex-of-refraction field to botain a numerical estimater of the optical disturbances.

23 Claims, 4 Drawing Sheets

204 FIRST SOFTWARE MODULE - CFD PROGRAM

208 SECOND SOFTWARE MODULE - RAY TRACING PROGRAM

210 INTERPOLATION SUBROUTINE

212 SHOCK WAVE PROFILE SUBROUTINE

206 PROCESSOR

METHOD AND SYSTEM FOR EVALUATING OPTICAL DISTURBANCES OCCURRING IN A SUPERSONIC FLOW FIELD

FIELD AND BACKGROUND OF THE INVENTION

The impact of aerodynamic flow on the performance of an airborne optical system is becoming a critical issue in the development and engineering of IR-electrooptic (EO) systems. The analysis of this impact is now at the forefront of IR-EO system research, and a significant effort has been made on this issue in recent years. For a good exemplary overview of the topic, see G. W. Sutton, "Aero-optical Foundations and Applications", AIAA Journal, vol. 25, No. 10, October 1985, p. 1525.

FIG. 1 illustrates the problem addressed by the present invention. Specifically, FIG. 1 shows a navigation pod 10 suspended below a wing 11 of an aircraft flying at supersonic speed. The front of pod 10 is a transparent dome 12. Mounted within pod 10 is an EO system 14 that captures and processes images of the surrounding environment ahead of pod 10. (The portion of EO system 14 that is invisible from outside pod 10 is shown in phantom.) In supersonic flight of aerodynamic bodies such as pod 10, the air surrounding dome 12 is heated and compressed significantly, and the flow becomes turbulent. These effects cause changes in the local index of refraction of the medium or "flow field" 16 surrounding EO system 14, and lead to optical aberrations that affect detector performance, and with it, the performance of pod 10. These aberrations include a mean shift in image position ("boresight error") together with mean blur that is represented as a mean field modulation transfer function $MTF_{MF}$, and turbulence related effects, mainly image spread blur represented as a turbulence modulation transfer function $MTF_t$. All three of these aberrations have to be calculated so that they can be taken into account accurately in system engineering and possibly removed through compensating measures.

Heretofore, optical aberrations in a flow field have been computed by using a computational fluid dynamics (CFD) program to compute the corresponding density field, followed by conversion of the density field to an index-of-refraction field. Then, using the "thin film" approximation, the index of refraction is integrated along a set of straight parallel rays through the flow field to obtain propagation phase differences along these rays. These phase differences indicate the extent to which an initially plane wave is distorted (blur) and tilted (boresight error) by propagation through the flow field. In practice, however, the use of an approximation that assumes straight parallel rays produces estimates of the optical aberration that are insufficiently accurate.

Ray tracing through an inhomogeneous optical medium is well-known in the art, and is used, for example, in the design of lenses. In principle, ray tracing code could be included in a CFD program to provide numerically accurate estimates of the optical aberrations. This, however, would require great skill on the part of the programmer, who would have to be expert in computational optics to be able to anticipate and deal with the various numerical instabilities that would arise during the ray tracing calculations, as is known in the art.

There is thus a widely recognized need for, and it would be highly advantageous to have, a method for calculating and compensating for optical disturbances occurring in a supersonic flow field that does not use embedded ray-tracing in a CFD program, does not use a thin-screen approximation, and therefore does not suffer from the prior art disadvantages listed above.

SUMMARY OF THE INVENTION

The present invention is of a method of evaluating optical disturbances occurring in a supersonic flow field, and for a system used to implement the method. Specifically, the method and system of the present invention use separate, commercially available CFD and ray tracing programs to calculate the optical disturbances and output compensating parameters. The different data formats of the two programs are dealt with by using an interpolation subroutine that is called by the ray tracing program to interpolate the index-of-refraction data on the grid used by the CFD program.

The present method is applicable to evaluating optical disturbances in the flow field around any aerodynamic platform traveling at supersonic speeds. Examples of such platforms include missiles, airborne target pods and airborne navigation pods.

According to the present invention there is provided a method of evaluating optical disturbances occurring in a flow field around a solid body, including the steps of: (a) performing a computational fluid dynamics (CFD) calculation to obtain a three-dimensional index-of-refraction field outside the solid body; and (b) performing at least one ray tracing calculation based on the index-of-refraction field to obtain a numerical estimate of the optical disturbances.

According to a preferred embodiment of the method of the present invention, the CFD calculation is performed with a numerical computer CFD program, and the step of performing separate ray tracing calculations is performed with a numerical computer ray tracing program separate from the CFD program.

According to a particular feature in the preferred embodiment of the method of the present invention, the CFD calculation includes the substep of calculating a three-dimensional density field and translating the density field into the index-of-refraction field.

According to another particular feature in the preferred embodiment of the method of the present invention, the index-of-refraction field is defined on a grid related to the flow field, and the step of performing ray tracing calculations includes interpolating the index-of-refraction field on the grid. Preferably, the interpolating is effected using a modified Shepard method.

According to yet another particular feature in the preferred embodiment of the method of the present invention, the CFD calculation includes obtaining a plurality of two-dimensional density data fields, and using a text editor to create the three-dimensional index-of-refraction field from the plurality of two-dimensional density data fields.

According to yet another particular feature in the preferred embodiment of the method of the present invention, the numerical estimate of the optical disturbance includes a modulation transfer function and/or a point spread function.

According to yet another particular feature in the preferred embodiment of the method of the present invention, the CFD calculation also produces output related to flow field turbulence, and the ray tracing calculations are performed in a manner that takes the turbulence into account. Preferably, the turbulence related output includes a three-dimensional index-of-refraction standard-deviation field outside the solid body and a correlation length of the flow field. Preferably, the turbulence is accounted for by forming a plurality of instances of the index-of-refraction field that are statistically consistent with the turbulence, and performing a respective ray tracing calculation for each instance of the index-of-refraction field. Each ray tracing calculation produces a respective numerical estimate of the optical disturbance. These respective numerical estimates are averaged to produce a final numerical estimate of the optical disturbance.

According to the present invention there is provided a system for evaluating flight induced optical disturbances occurring in a flow field around a solid body, including (a) a memory for storing: (i) a first software module that computes refractive index data related to the flow field; and (ii) a second software module, separate from the first software module, that receives as input the refractive index data, and creates in response a numerical estimate of the optical disturbances, and (b) a processor for performing the refractive index computation using the first software module and for creating the numerical estimate using the second software module.

According to a preferred embodiment of the system of the present invention, the second software module includes a first subroutine for interpolating the refractive index data at an arbitrary point within the flow field to obtain a value of the refractive index at the arbitrary point. Most preferably, the first software module also computes a shock wave profile, and the second module also includes a second subroutine for inputting the shock wave profile, the first subroutine then interpolating the refractive index data in accordance with the shock wave profile.

According to a particular feature in the preferred embodiment of the system of the present invention, the first software module includes a computational fluid dynamics (CFD) program, and the second module includes a ray-tracing program. Preferably, the CFD program and the ray-tracing programs are commercially available programs. Most preferably, the CFD program is Fluent6 and the ray-tracing program is CodeV.

According to the present invention there is provided a method of designing an optical system of a flying body, including the steps of: (a) evaluating optical aberrations occurring in a flow field around the flying body by steps including: (i) performing a computational fluid dynamics calculation to obtain a three-dimensional index-of-refraction field outside the flying body, and (ii) performing at least one ray tracing calculation based on the index-of-refraction field to obtain a numerical estimate of the optical aberrations; and (b) optimizing a design of the at least one optical element of the optical system in accordance with the optical aberrations.

In other words, the scope of the present invention includes the use of the calculational method of the present invention in the design of an EO system. The design of the optical elements (for example the lenses) of the system is optimized in accordance with the calculated optical aberrations. The scope of the present invention also includes the EO system so designed.

BRIEF DESCRIPTION OF THE DRAWINGS

The invention is herein described, by way of example only, with reference to the accompanying drawings, wherein:

FIG. 3 is a block diagram of a system for calculating and compensating for optical disturbances occurring in a supersonic flow field according to the present invention;

DESCRIPTION OF THE PREFERRED EMBODIMENTS

The present invention is of a method of evaluating optical disturbances occurring in a supersonic flow field. Specifically, the present invention can be used to correct for mean flow effects and for turbulence using an innovative, synergistic combination of a CFD program and a ray-tracing program. Unlike prior art ray-tracing programs that are normally embedded in CFD routines, the ray tracing program used herein is not based on a thin-screen approximation.

In general terms, the method is based on commercially available software, specifically a regular ray-tracing program named "CodeV", available from Optical Research Associates of Pasadena, Calif., USA, and a CFD program named "Fluent6", available from Fluent Inc., Lebanon, N.H., USA. The method disclosed herein obtains a three-dimensional density ("p") field out of the CFD program on a nonuniform grid that is numerically optimal for CFD but that is suboptimal for numerically accurate ray tracing. The density values at the points of the CFD grid are translated into corresponding refractive index values to provide a three-dimensional refractive index field sampled at the points of the CFD grid. A subroutine is provided that the ray-tracing program calls to interpolate the refractive index field, as sampled on the CFD grid, to the points at which the ray-tracing program needs refractive index values in order to trace the rays.

Specifically, the method uses the CFD code to output optically relevant (density) data, which is then transformed into an index-of-refraction (IOR or "n") field. The density or IOR data does not have to be presented in an analytical form, and it is typically introduced in the most general form as a discrete non-uniform grid of points. A numerical interpolation method, preferably a modified quadratic Shepard method (Robert J. Renka, "Multivariate interpolation of large sets of scattered data", *ACM Transactions on Mathematical Software* vol. 14 no. 2 pp. 139–148 (June 1988)), is then used for the data interpolation, to adapt the CFD output data to the numerical requirements of the ray tracing program. This enables a simple interface with virtually any software output. Such compatibility makes sure that the method can be easily extended for the solution of a whole spectrum of optical problems that involve arbitrary IOR changes in the bulk, or arbitrary optical surface changes. For example, image quality degradation caused by dome heating can be easily assessed, with both IOR and dome shape distortion being taken into account. Other interpolation methods may be also used instead of the Shepard method.

The principles and operation of a method of compensating for optical disturbances occurring in a flow field according to the present invention may be better understood with reference to the drawings and the accompanying description.

Figure 1:
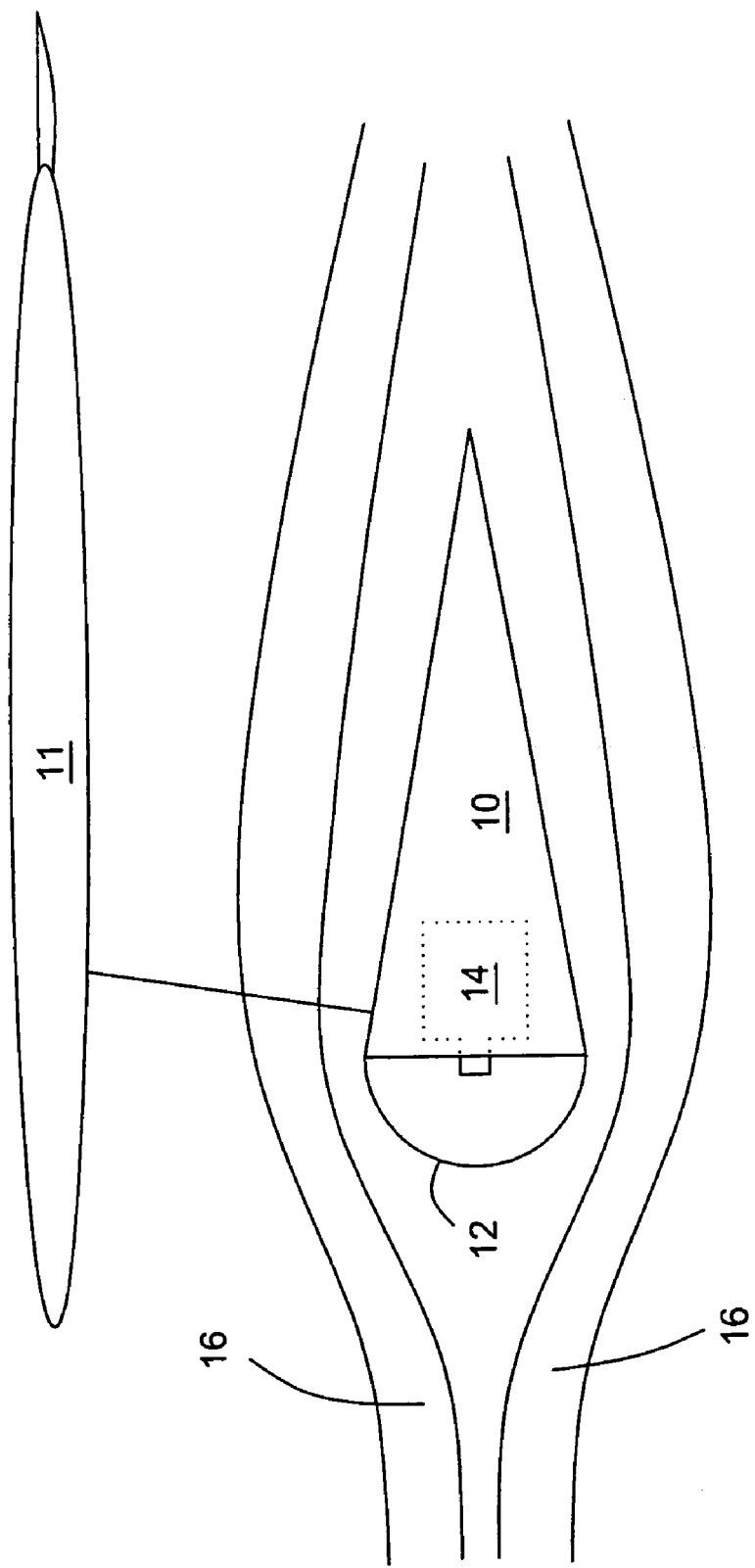
FIG. 1 illustrates a flow field around a transparent dome of a navigation pod of a supersonic aircraft.
Figure 2:
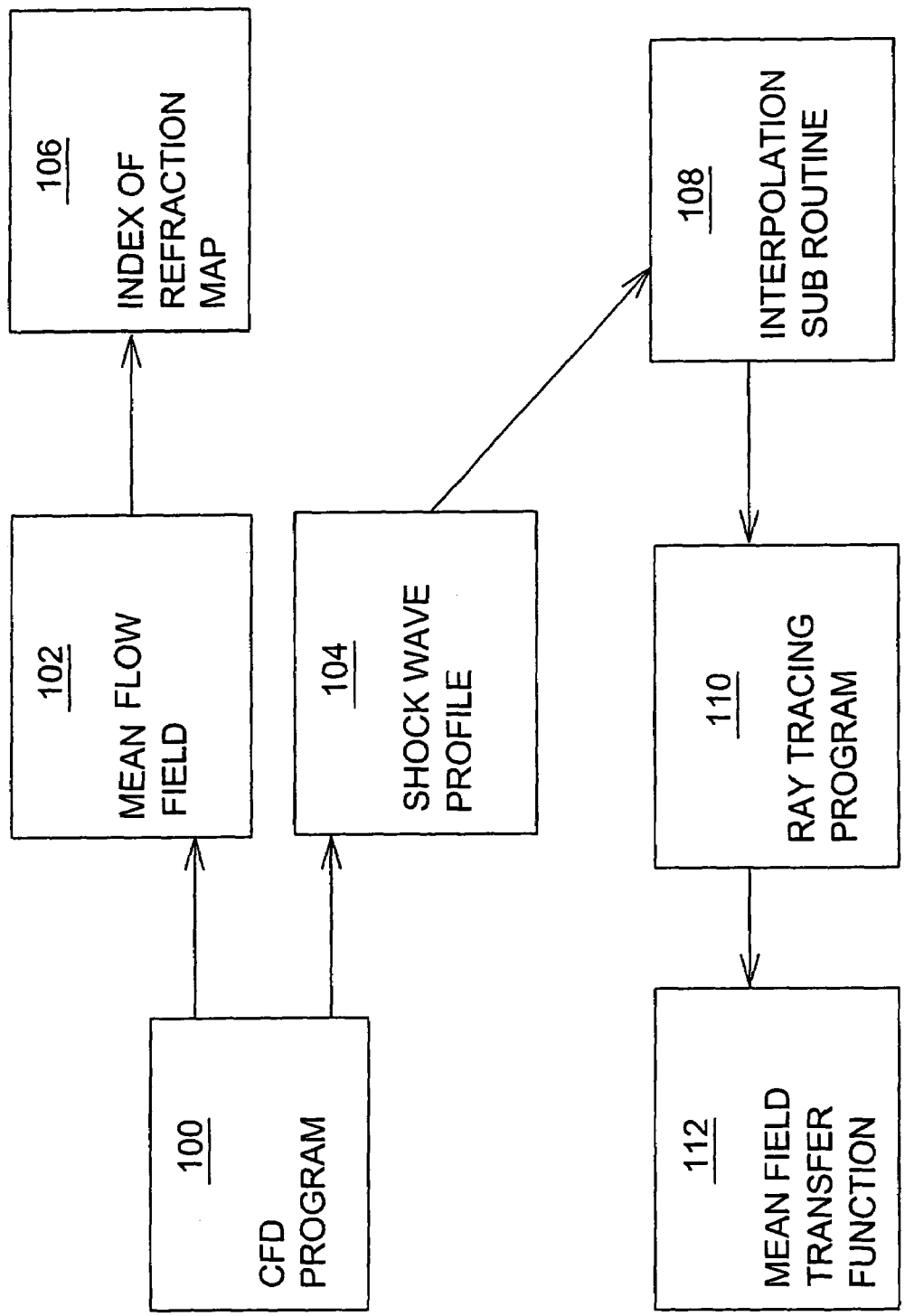
FIG. 2 is a flow chart of a preferred embodiment of the method of the present invention, as applied to mean flow.

Referring again to the drawings, FIG. 2 shows a flow chart of a preferred embodiment of the method of the present invention, as applied to mean flow. The main steps of the method are represented by various blocks. A CFD program (preferably Fluent6) 100 is used to calculate both a mean flow density field 102 sampled on a non-uniform grid, and a shock wave profile 104. Density field 102 is translated in an index-of-refraction map 106 on the same grid, preferably using the Gladstone-Dale formula (J. H. Gladstone and T. P. Dale, *Trans. Roy. Soc. London* vol. 153 pp. 317–337 (1863). An interpolation subroutine 108, preferably based on the modified Shepard interpolation method, is used to adapt the IOR data from the CFD grid to the dynamically computed, numerically optimized points at which a ray tracing program 110, preferably a CodeV program 110, needs IOR values. The interpolation takes shock wave profile 104 into account by interpolating only up to the two-dimensional boundary defined by shock wave profile 104. In other words, the two thee-dimensional subspaces on the two sides of shock wave profile 104 are two independent interpolation regimes. CodeV program 110 then calculates a mean field modulation transfer function $MTF_{MF}$ 112, preferably using Hopkins's method (H. H. Hopkins, "Geometrical-optical treatment of frequency response", *Proc. Phys. Soc.* Vol. 70B p. 1002 (1957)) for numerical evaluation of the auto correlation of the pupil function. Next, each of the steps are explained in more detail.

The three-dimensional density grid computed by Fluent6 is retrieved indirectly from Fluent6. As described in the Fluent manual dated December 2001, pp. 25-117 to 25-119, incorporated herein by reference, output available from Fluent6 includes "XY plot files". A portion of space intended for the aero-optics calculations is defined, and three such files are prepared as described in more detail in the manual: an <X, p> file, an >X, Y> file and an <X, Z> file, that sample the three dimensional grid on which Fluent6 computes the density field. A text editor is then used to create from the three data files above a <X, Y, Z, p> data file. The <X, Y, Z, p> data file is then translated into a <X, Y, Z, n> data file, using the Gladstone-Dale formula. Shock wave profile 104 is computed from the <X, Y, Z, p> data file by methods that are well-known in the art.

As discussed in the CodeV v.9.0 Reference Manual, Vol. 1 (September 2001) p. 2A-362 and p. 2A-431, the user of CodeV provides two subroutines for inputting an inhomogeneous and discontinuous index of refraction. Subroutine USERGRN computes the index of refraction n and the gradient of n (Vn) at an arbitrary point in space. Subroutine USERSUR defines a surface of discontinuity, such that the rays traced by CodeV, in accordance with the index of refraction computed by subroutine USERGRN, are diffracted at the surface of discontinuity. As described in the CodeV manual, these subroutines are intended for tracing rays through solid discontinuous inhomogeneous optical media such as gradient index material lenses. One of the innovative aspects of the present invention is the realization that these subroutines also can be used for tracing rays through a gaseous discontinuous inhomogeneous optical medium such as the flow regime around a supersonic body. In the context of the present invention, subroutine USERGRN reads the <X, Y, Z, n> data file and interpolates the data in that file to obtain values of n and Vn at an arbitrary point in space. Subroutine USERSUR defines the surface of discontinuity to follow the shock wave profile that is inferred from the Fluent6 output. Because CodeV traces rays with continuous curvatures only up to and from the surface of discontinuity, where the ray curvatures are discontinuous, USERGRN in effect interpolates independently on the two sides of the shock wave profile.

To account for turbulence in the flow field, more output is needed from the CFD program. Specifically, in addition to mean flow density field 102 and shock wave profile 104, the CFD program must produce a density standard-deviation field and a correlation length. The correlation length is a parameter that characterizes the eddy size of the turbulence. Given these additional outputs, a Monte Carlo method is used to produce a modified modulation transfer function that takes turbulence into account. The density standard-deviation field is transformed into a three-dimensional IOR standard deviation field, also preferably using the Gladstone-Dale formula. A set of separate instances of the IOR field are created that are statistically consistent with the mean flow IOR field, with the IOR standard deviation field and with the correlation length. For each instance of the IOR field, ray tracing program 110 is used to trace rays through that instance of the IOR field, as described above, to produce an associated instance of the point spread function of the system. These instances of the point spread function are averaged to produce an average point spread function. The final modulation transfer function that takes turbulence into account is the absolute value of the Fourier transform of this average point spread function, normalized to its zero spatial frequency component.

FIG. 3 is a block diagram of a system for calculating optical disturbances occurring in a supersonic flow field according to the present invention. System 200 includes a memory 202 for storing a first software module 204 that computes refractive index data related to the flow field. Module 204 includes a CFD program, preferably a commercial CFD program, and most preferably the Fluent6 program. Module 204 is connected to a processor 206 that runs the CFD program to calculate mean flow density data on a three-dimensional grid, and translates the mean flow density data to index-of-refraction data on the same grid. Module 204 also computes and outputs a shock wave profile of the flow field. Memory 202 also stores a second software module 208, separate from first module 204, that receives as input the refractive index data on the grid, and creates in response a numerical estimate of the optical disturbances. Module 208 includes a ray-tracing program, preferably a commercial program and most preferably the CodeV ray-tracing program. The ray-tracing program is preferably run on processor 206. Optionally, it may be run on a separate processor (not shown) included in system 200. Module 208 includes two user-defined subroutines for the ray-tracing program: an interpolation subroutine 210 and a shock wave profile input subroutine 212. Interpolation subroutine 210 is used by module 208 to interpolate the refractive index data on the grid as needed. Preferably, these interpolations are done using the modified Sheppard method. Module 208 also receives as input, via shock wave profile input subroutine 212, the shock wave profile computed by module 204; and the interpolations performed by interpolation subroutine 208 are bounded by the shock wave profile.

As noted above, the scope of the present invention includes a method of designing EO system 14 to compensate for the optical aberrations in flow field 16. Methods for the design of optical elements, such as lenses, of EO system 14, are well-known in the art. See, for example, Warren J. Smith, *Modern Optical Engineering* (McGraw Hill, 2000). It is straightforward for those skilled in the art to use the principles discussed therein to design the optical elements of EO system 14 to compensate for the optical aberrations introduced by flow field 16.

EXAMPLE

Figure 4:
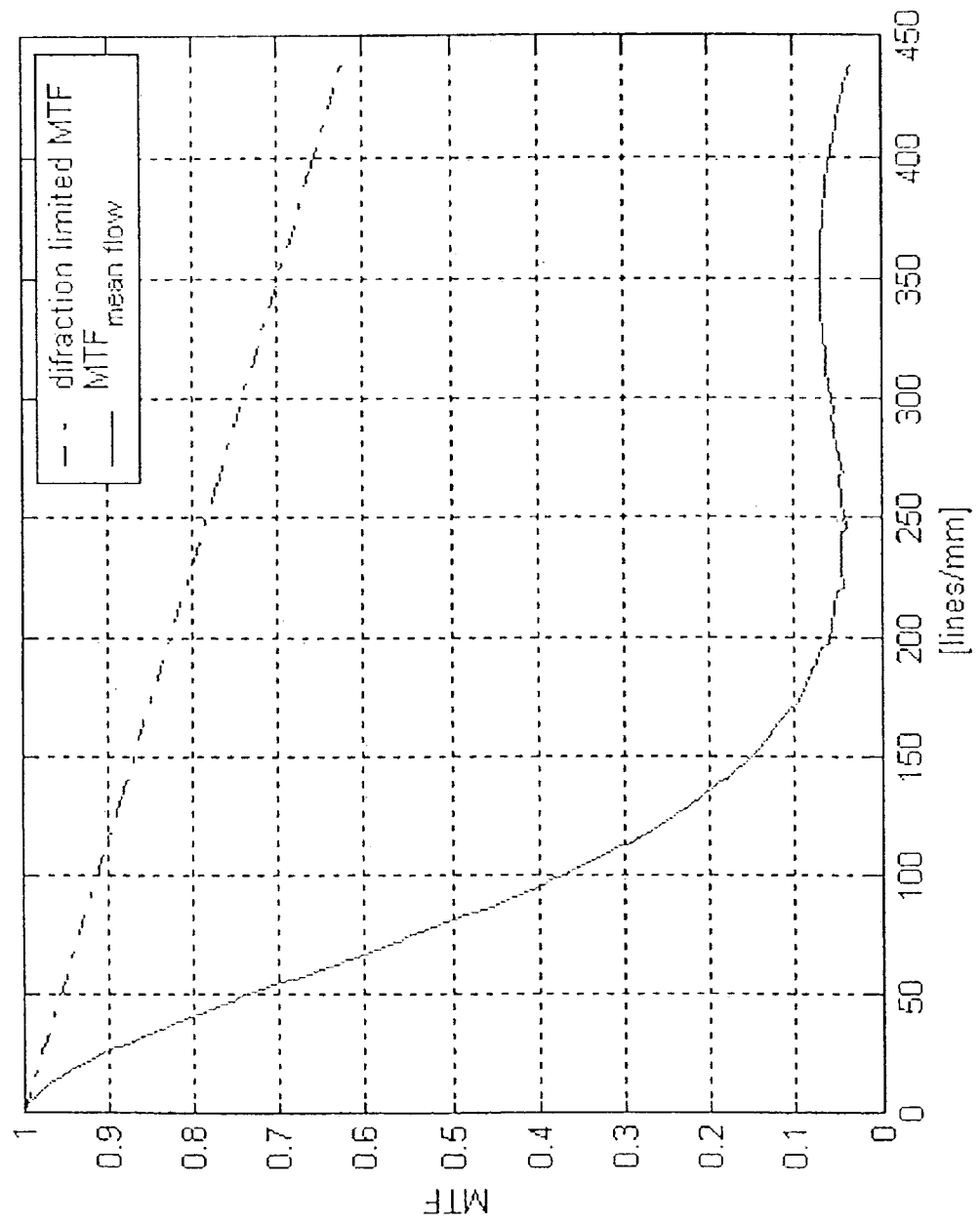
FIG. 4 shows a comparison of $MTF_{MF}$, as computed according to the present invention, vs. the diffraction limited MTF, for the system of FIG. 1.

FIG. 4 shows aero-optical calculations performed according to the present invention for pod 10, with a 14 mm diameter hemispherical dome 12, moving at Mach 2. The CFD calculations were performed using Fluent6, assuming standard atmospheric conditions, 3D viscous flow, and a regular k-ε model with wall functions. The CFD calculations were checked to insure independence of mesh size, and were performed to a residual level of $10^3$. The velocity vector of pod 10 was assumed to be parallel to the optical axis of EO system 14, so that there was no boresight error. In the CodeV calculations, an ideal lens with a focal length of 14 mm was placed immediately behind dome 12 so that the calculations captured only the degradations caused by the aero-optic effect. Specifically, FIG. 4 shows $MTF_{MF}$ vs. MTF in the diffraction limit. The significant degradation of $MTF_{MF}$ relative to the diffraction limit MTF shows that aero-optical phenomena cannot be neglected when EO system 14 needs to provide high resolution images.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described with respect to a limited number of embodiments, it will be appreciated that many variations, modifications and other applications of the invention may be made.

What is claimed is:

1. A method of evaluating optical disturbances occurring in a flow field around a solid body, comprising the steps of:
   (a) performing a computational fluid dynamics (CFD) calculation to obtain a three-dimensional index-of-refraction field outside the solid body; and
   (b) performing at least one ray tracing calculation based on said index-of-refraction field to obtain a numerical estimate of the optical disturbances.

2. The method of claim 1, wherein said CFD calculation is performed with a numerical computer CFD program, and wherein said at least one ray tracing calculation is performed with a numerical computer ray tracing program separate from said CFD program.

3. The method of claim 1, wherein said CFD calculation includes the substeps of calculating a three-dimensional density field and translating said density field into said index-of-refraction field.

4. The method of claim 1, wherein said index-of-refraction field is defined on a grid related to the flow field, and wherein said at least one ray tracing calculation includes interpolating said index-of-refraction field on said grid.

5. The method of claim 4, wherein said interpolating is effected using a modified Shepard method.

6. The method of claim 1, wherein said CFD calculation includes obtaining a plurality of two-dimensional density data fields and using a text editor to create said three-dimensional index-of-refraction field from said plurality of two-dimensional density data fields.

7. The method of claim 1, wherein said numerical estimate of the optical disturbances includes a modulation transfer function.

8. The method of claim 1, wherein said numerical estimate of the optical disturbances includes a point spread function.

9. The method of claim 1, wherein said CFD calculation also provides a shock wave profile, and wherein said ray tracing calculation is based on both said index-of-refraction field and on said shock wave profile.

10. The method of claim 1, wherein said CFD calculation also produces output related to a turbulence of the flow field, and wherein a plurality of said ray tracing calculations are performed in a manner that accounts for said turbulence.

11. The method of claim 10, wherein said output related to said turbulence includes:
    (i) a three-dimensional index-of-refraction standard-deviation field, and
    (ii) a correlation length of the flow field.

12. The method of claim 10, wherein said turbulence is accounted for by steps including:
    (i) forming a plurality of instances of said index-of-refraction field that are statistically consistent with said output related to said turbulence;
    (ii) for each said instance of said index-of-refraction field, performing a respective said ray tracing calculation to obtain a respective instance of said numerical estimate of the optical disturbance; and
    (iii) averaging said respective instances of said numerical estimate of the optical disturbance.

13. A system for evaluating flight induced optical disturbances occurring in a flow field around a solid body, comprising
    (a) a memory for storing:
        (i) a first software module that computes refractive index data related to the flow field; and
        (ii) a second software module, separate from said first software module, that receives as input said refractive index data, and creates in response a numerical estimate of the optical disturbances, and
    (b) a processor for performing said refractive index computation using said first software module and for creating said numerical estimate using said second software module.

14. The system of claim 13, wherein said second software module includes a first subroutine for interpolating said refractive index data at an arbitrary point within the flow field to obtain a value of said refractive index at said arbitrary point.

15. The system of claim 14, wherein said first software module also computes a shock wave profile, and wherein said second software module includes a second subroutine for inputting said shock wave profile, said first subroutine then interpolating said refractive index data in accordance with said shock wave profile.

16. The system of claim 13, wherein said first software module includes a computational fluid dynamics (CFD) program, and said second module includes a ray-tracing program.

17. The system of claim 16, wherein said CFD program and said ray-tracing programs are commercially available programs.

18. The system of claim 17, wherein said commercially available CFD program is a Fluent6 program, and wherein said ray-tracing program is a CodeV program.

19. The system of claim 13, wherein said numerical estimate includes a modulation transfer function.

20. The system of claim 13, wherein said numerical estimate includes a point spread function.

21. A method of designing an optical system of a flying body, comprising the steps of:
    (a) evaluating optical aberrations occurring in a flow field around the flying body by steps including:
        (i) performing a computational fluid dynamics calculation to obtain a three-dimensional index-of-refraction field outside the flying body; and (ii) performing at least one ray tracing calculation based on said index-of-refraction field to obtain a numerical estimate of said optical aberrations; and (b) optimizing a design of said at least one optical element of the optical system in accordance with said optical aberrations.

22. The method of claim 21, wherein one of said at least one optical element is a lens.

23. An optical system designed in accordance with claim 21.

* * * * *